United States Patent [19]

Rusz

[11] Patent Number: 4,637,385
[45] Date of Patent: Jan. 20, 1987

[54] PULMONARY VENTILATOR CONTROLLER

[76] Inventor: Tibor Rusz, 761 West St., Pittsfield, Mass. 01201

[21] Appl. No.: 818,005

[22] Filed: Jan. 13, 1986

[51] Int. Cl.$^4$ ............................................. A61M 16/00
[52] U.S. Cl. .......................... 128/204.21; 128/205.14; 128/205.15; 128/205.24
[58] Field of Search ...................... 128/204.21, 204.23, 128/204.25, 204.22, 205.11, 205.13, 205.14, 128/205.15, 205.16, 205.18, 203.14, 205.24

[56] References Cited

U.S. PATENT DOCUMENTS

| | | | |
|---|---|---|---|
| 2,754,819 | 7/1956 | Kirschbaum | 128/204.23 |
| 2,888,922 | 6/1959 | Bellville | 128/204.23 |
| 4,036,221 | 7/1977 | Hillsman et al. | 128/204.23 |
| 4,256,100 | 3/1981 | Levy et al. | 128/205.15 |
| 4,323,064 | 4/1982 | Hoenig et al. | 128/204.21 |
| 4,340,044 | 7/1982 | Levy et al. | 128/205.15 |
| 4,587,967 | 5/1986 | Chu et al. | 128/204.21 |

FOREIGN PATENT DOCUMENTS 3416291 3/1985 Fed. Rep. of Germany ......................... 128/204.23

Primary Examiner—Henry J. Recla
Attorney, Agent, or Firm—Arthur K. Hooks

[57] ABSTRACT

A pulmonary ventilator system has a bellows assembly and a source of driving gas connected by a series branch including an electrically-controlled switching valve and a motor-controlled flow-rate-controlling valve. A controller including a microprocessor senses the position of the flow-rate-controlling valve via a mechanical to electrical transducer and has outputs connected to and controlling the switching valve and the motor. It has programmed in its memory the maximum flow rate capacity of the flow-rate-controlling valve and the maximum capacity of the bellows. The microprocessor is capable of receiving from an operator his target values for minute volume, breathing rate and expiration time to inspiration time ratio. When the combination of these target values predict a flow rate or a tidal volume greater than the capacity of the flow-controlling valve and or greater than the bellows can handle, it reinstructs the ventilator system to employ a new and realizable value of breathing rate and/or expiration time to inspiration time ratio. The actual operating parameters realized by the controller are displayed.

4 Claims, 7 Drawing Figures

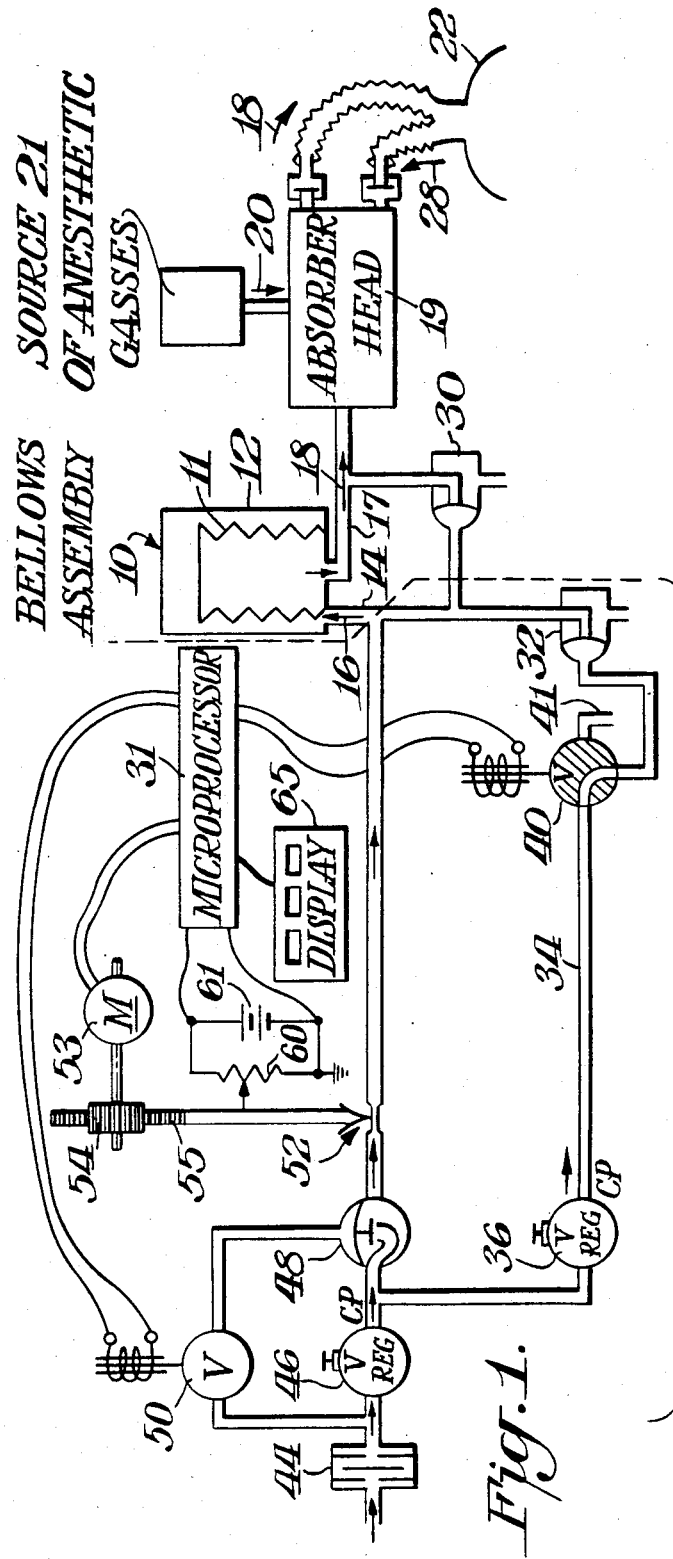
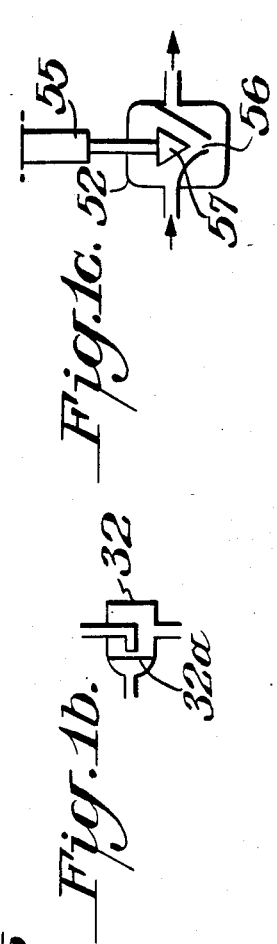
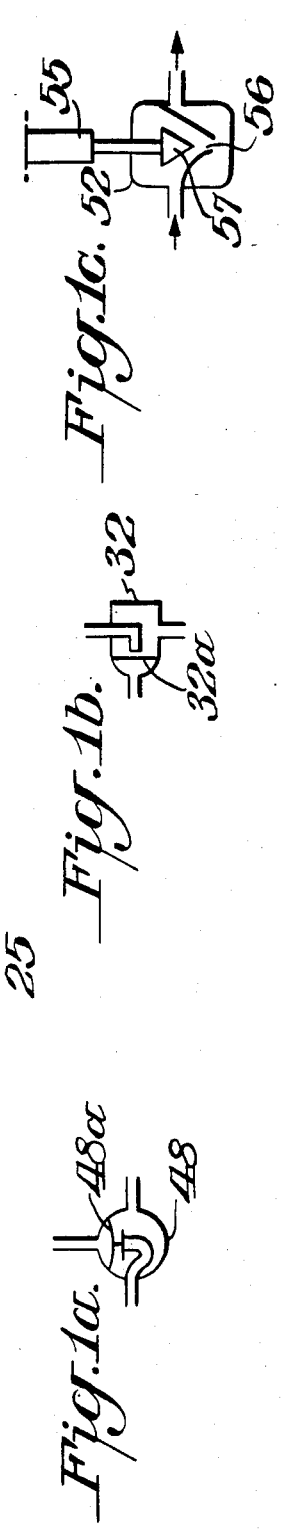

4,637,385

PULMONARY VENTILATOR CONTROLLER

BACKGROUND OF THE INVENTION

This invention relates to a pulmonary ventilator controller system for use by an anesthesiologist to ventilate the lungs of a paralyzed and anesthetized patient undergoing surgery, and more particularly relates to such a controller that is capable of automatically altering the target values dialed in by the anesthesiologist for breathing rate and inspiration time to make them compatible with the maximum flow rate and maximum capacity of the ventilator being controlled.

In a pulmonary ventilator system of the prior art, the anesthesiologist-operator is required to orchestrate the control of the separate ventilator operating parameters, e.g. driving gas flow rate, breathing rate, expiration times and inspiration time to achieve a desired delivery rate of breathing gas. Breathing gas delivery rate is called minute volume and is usually measured in liters per minute. When using a prior art ventilator such as that described in my patent application Ser. No. 685,906, filed Dec. 24, 1984, wherein the minute volume of the breathing gas is also equal to the total amount of driving gas provided each minute, an oscillator periodically turns on and off a solenoidally actuated valve in the input line supplying the driving gas to the ventilator. The anesthesiologist separately adjusts a driving gas flow rate determining valve, the breathing rate by adjusting the frequency of the oscillator and the ratio of expiration time to inspiration time by adjusting the duty factor of the oscillator. It is easily possible to make the mistake of making a combination of these adjustments that would call for a greater flow rate than the driving gas source can actually provide, or call for a tidal volume larger than the capacity of the ventilator.

It is therefore an object of the present invention to provide a pulmonary ventilator controller that is simpler to operate and is safer and more reliable in use.

SUMMARY OF THE INVENTION

This invention contemplates a method for controlling a pulmonary ventilator assembly that is especially well suited for being effected semi-automatically. It includes determining, from a consideration of a particular patient's needs, the target values for the minute volume $MV_T$, the breathing rate $R_T$, and the ratio of expiration time to inspiration time $E_T/I_T$. The semi-automatic ventilator system includes a source of constant-pressure driving gas and a pulmonary bellows ventilator assembly. A switching valve and a throttling valve are connected in series between the driving-gas source and the ventilator. The switching valve opens and shuts periodically at a rate for determining the target breathing rate and for determining the target $E_T/I_T$ ratio. The throttling valve is adjusted to produce the flow rate that provides the target minute volume $MV_T$.

Now, when these target values result in a tidal volume TV greater than the maximum capacity $TV_{max}$ of the bellows, the frequency of breathing is changed to a value $R_A$ by adjusting the switching rate of the switching valve such that $R_A = M_T/TV_{max}$ providing the closest $R_A$ to $R_T$ that is possible while maintaining the target $MV_T$ and using the full capacity of the bellows.

Similarly this method preferably includes readjusting the inspiration time I away from $I_T$ to a value $I_A$ whenever the target values $M_T$, $E_T/I_T$ and $R_T$ would result in a flow rate F that exceeds $F_{max}$ such that $$I_A = \frac{MV_T}{R_T F_{max}}.$$

Furthermore, safety and convenience is further enhanced by displaying the actual values for the parameters MV, R and E/I at all times.

BRIEF DESCRIPTION OF THE DRAWINGS

FIG. 1 shows a diagram of the preferred embodiment of the pulmonary ventilator system with a controller of this invention.

FIGS. 1a, 1b and 1c show in more detail diagrams of two of the pneumatically controlled valves and the flow-rate controlling valve that are included in the diagram of FIG. 1.

DESCRIPTION OF THE PREFERRED EMBODIMENTS

Figure 2:
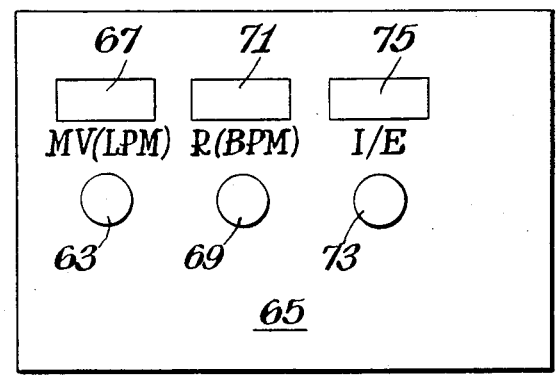
FIG. 2 shows a front panel including display windows and manual parameter dials that may be used with the controller of FIG. 1.

A bellows assembly 10 illustrated in FIG. 1 has a bellows 11 enclosed in a housing 12. When a driving gas 16 flows through pipe 14 into the chamber between bellows 11 and housing 12, the bellows compresses and forces the breathing gas 18 through pipe 17 through the absorber head 19 carrying anesthetic gasses 20 from the anesthetic gas source 21 into the shroud 22 that may be coupled to the patient's breathing system (not shown). The bellows 11 isolates the patient's breathing system from the controller 25 which includes all of the elements shown to the left of the dashed line in FIG. 1. The bellows 11 transmits all pressure and volume changes generated by the controller to the patient's breathing system. The pressure inside the bellows is essentially the same as that on the outside of the bellows. During an inspiratory period, the amount of gas 18 delivered from the bellows 11 to the patient is the same as the amount of gas 16 delivered by the control unit to the bellows assembly 10. During an expiratory period, the process is reversed and the gas flowing from the patient's contracting elastic lungs into the bellows causes the same quantity of gas as was forced into the lungs during the inspiratory period to be expelled through controller pipe 14 as the bellows fills and expands.

This invention recognizes that among all of the parameters of concern in the control of pulmonary ventilation the so-called minute volume MV, is of greatest importance. MV is the amount of gas inhaled or exhaled in one minute. The anesthesiologist establishes a delivery rate MV appropriate for the anticipated needs of the patient.

At the very end of each expiratory period, the bellows 11 will reach the mechanical limit of its excursion and the pop off valve 30 will open to exhaust the excess. This exhausted excess is approximately equal to the volume of fresh gas 20 addition to the inspiratory gas 18.

The pop-off valve 30 is preferably built into the base of the bellows assembly as described in detail in my co-pending application Ser. No. 685,906 filed Dec. 24, 1984. Pop-off valve 30 is a pneumatically controlled threshold type valve. In this instance, the driving gas pressure in pipe 14 holds the valve closed during the inspiratory period.

Another pneumatically controlled threshold type valve 32 is held closed by pressurized air from regulator 36 during the inspiratory period and held open, dropping the pressure in pipe 14 to zero, during the expiratory period. Thus during the expiratory period the pop-off threshold pressure for valve 30 is low, e.g. near ambient, and relatively high during the inspiratory period, e.g. 1 p.s.i. over ambient.

The upper threshold pressure in discharge valve 32 must be carefully and reliably controlled because that is the pressure that sets a safe limit beyond which forced inspiratory gasses may not be applied to the patient's breathing system. Too high a pressure can easily rupture the lungs.

The pressure in pipe 34 is regulated for that purpose by pressure-regulating valve 36 set at a predetermined pressure.

The electrically controlled 3-way valve 40 between pipe 34 and the valve 32 opens (as shown) to raise the discharge threshold pressure of valve 32 and closes to allow the pressure in the controlled side of valve 32 to drop to zero by passing out the tube 41.

A source (not shown) of compressed air or oxygen is applied through a filter 44 to a standard pressure regulator valve 46. The output of regulator valve 46 is connected to yet another penumatically controlled valve 48 and to the input of regulator valve 36. An electrically controlled valve 50 when opened closes valve 48. Valve 48 is followed by a continuously variable type gas flow rate controlling valve 52. This valve 52 has a reversible motor 53, driving a pinion gear 54 and driving in turn a gear rack 55. The valve 52 may include an orifice 56 depicted in FIG. 1c and a conical plunger 57 fitted therein so that when the plunger 57 is gradually withdrawn from the orifice 56 the valve restriction to the flow of gas is reduced correspondingly. The rack gear 55 is connected to the plunger 57 so that the motor 53 draws out the plunger 57 when operated in one direction and inserts the plunger 57 to reduce the flow rate when operated in the other (rotational) direction.

The gear rack 55 is also mechanically connected to the arm of a potentiometer 60 across which potentiometer a DC voltage from a voltage source 61 is applied. The voltage developed at the potentiometer arm is a known measure of the gas flow rate through the valve 52 when the constant gas pressure at the output of pressure regulator valve 46 is known.

In the controller 25 of this invention, the desired or target minute volume, $MV_T$, can be dialed in directly by turning a first knob 63 located at the left of the front panel 65 as seen in FIG. 2. The $MV_T$ dialed in is displayed in the left window 67.

The anesthesiologist operator also dials in the target breathing frequency $R_T$ by turning a second knob 69. The actual frequency R realized is displayed at all times at the front panel window 71 in breaths per minute (BPM). For the target values of $MV_T$ and $R_T$, the tidal volume, TV, will foretold by the relationship TV=MV/R. However, it is inevitable that on some occasion the operator will unwittingly determine a value for TV that exceeds the capacity of the bellows of the pulmonary ventilator.

In this system, the patient's breathing is totally controlled by the controller 25. The maximum bellows capacity establishes the maximum tidal volume, $TV_{max}$. The standard adult size ventilator bellows capacity is 1.5 liters. That information is put in the memory of the controller microprocessor 33 (as is also the maximum capacity, 300 ml, of the pediatric size bellows). The microprocessor determines what tidal volume TV is foretold according to the dialed-in-target values MV and R by the relationship TV=MV/R. If this TV is greater than $TV_{max}$ the controller adjusts the breathing frequency R upward beyond that which was dialed in until the 1.5 liters ($TV_{max}$) is reached, and displays in the display window 71 the actual frequency $R_A$ at which the assisted breathing is occuring, as determined by the controller $$R_A = \frac{MV_T}{TV_{max}}.$$

Therefore the controller 25 is capable of overriding the operator instructions as to breathing frequency R, to always follow the crucial minute-volume instructions, and advises the operator of the actual breathing frequency that has been established.

Thus far, in the operation of this system, MV and R are now established. Not only is the tidal volume known but the relationship E+I=I/R is by definition of these factors an established limitation on the values of E and I. However, none of the values are fully established or foretold by inspiration time I, expiration time E (or the ratio I/E), nor flow rate F.

Keeping in mind that flow rate F is non zero only during the inspiration period, then the following relationship holds:

$$I = MV/RF.$$

These machine determined relationships are all programmed into the microprocessor. So is $F_{max}$ the maximum flow rate capability of the metering valve 52.

The controller 25 of the preferred embodiment is so contructed that a third knob 73 on the front panel varies the inspiration time being determined by a clock generator (not specifically shown) in the microprocessor 31. When the desired or target value for the ratio I/E is dialed in, as observed by the number in the display window 75, by adjusting knob 73, it is clearly possible that the foretold value for F will exceed $F_{max}$ and the machine cannot comply. The controller recognizes this condition and readjusts the inspiration time to $I_A$ such that $$I_A = \frac{MV_T}{R_T F_{max}}$$

unless $R_T$ had been already readjusted to $R_A$ to be compatible with $TV_{max}$ in which case $$I_A = \frac{TV_{max}}{F_{max}}.$$

The resulting relationships for the ratio of expiration to inspiration time $$\frac{E_A}{I_A} = \frac{F_{max}}{MV_T} - 1$$

is then displayed in window 75 reflecting the actual ratio being effected by the controller.

Figure 3:
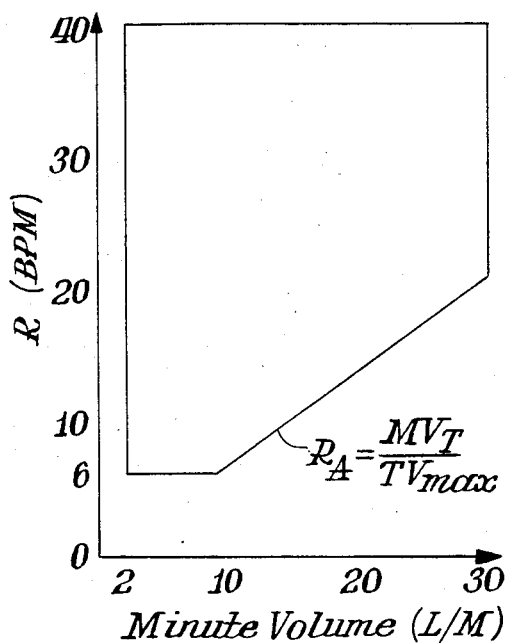
FIG. 3 shows a plot exhibiting the operating limit coordinates of minute volume and breathing rate of a controller of this invention having been programmed for use with a particular bellows and driving gas system.
Figure 4:
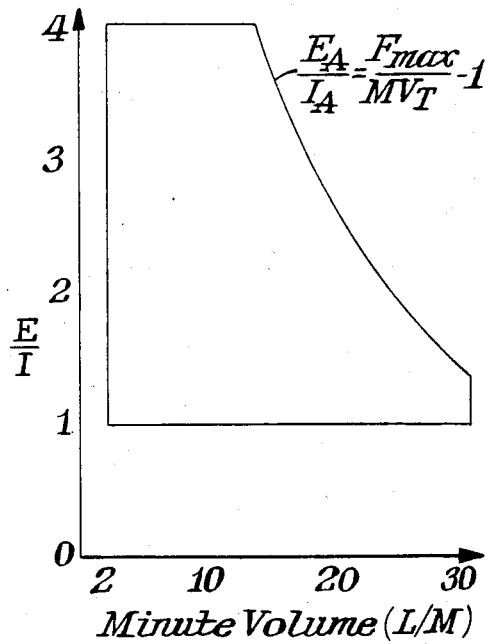
FIG. 4 shows a plot exhibiting the operating limit coordinates of expiratory time to inspiratory time ratio and minute volume of a controller of this invention having been programmed for use in a particular ventilator.

The machine limitations recognized and compensated for by the controller through automatic readjustments are depicted in FIGS. 3 and 4. In any and all situations the controller displays the operating parameters actually effected in display windows 67, 71 and 75, so that the anesthesiologist always knows what in reality is occuring.

In FIG. 3, a particular ventilator operating range permitted by the companion controller of this invention is shown wherein the sloped straight line limit is determined by maximum ventilator capacity ($TV_{max}$) of 1.5 liters.

That straight line is mathematically given by $$R_A = \frac{MV_T}{TV_{max}} = \frac{MV_T}{1.5}.$$

The same ventilator and controller has an operating range further restricted as shown FIG. 4 wherein the curved line segment is determined by the maximum flow rate of the controlling valve (52) to be 70 liters per minute assuming that the regulator (46) establishes the driving gas pressure at 25 p.s.i. that curved line is mathematically given by $$\frac{E_A}{I_A} = \frac{F_{max}}{MV_T} - 1 = \frac{70}{MV_T} - 1.$$

The controller also limits breathing rate to within 6 and 40 breaths per minute and limits the expiration to inspiration time ratio to within 1 and 4 as indicated in FIGS. 3 and 4.

What is claimed is:

1. A pulmonary-bellows-ventilator system for controlling the breathing of an anesthetized and paralyzed patient undergoing surgery, comprising a pulmonary-bellows assembly having a housing, a bellows mounted within said housing forming a chamber therebetween, an inlet on said housing fluidically communicating with said chamber and an outlet means on said housing fluidically communicating with the interior of said bellows and for delivering gas to a patient said bellows having a maximum tidal volume, $TV_{max}$, a constant-pressure driving-gas source; a switchable valve and an electrically controllable variable throttling valve, said valves connected in series from the output of said source to the input of said bellows assembly, said source and said throttling valve establishing together a maximum flow rate, $F_{max}$, of said driving gas through said throttling valve; instruction input means for providing target values of the minute volume, MV, of driving gas delivered each minute from said source to said bellows assembly, the frequency, R, at which said switchable valve is opened and closed, the flow rate, F, of driving gas through said throttling valve during periods when said switchable valve is open, and the quantities $F_{max}$ and $TV_{max}$, microprocessor means having inputs connected to said instruction input means for accepting and storing said target values, said microprocessor means having outputs connected to said switchable valve and said throttling valve, for establishing the actual frequency R, flow rate F and inspiration time I that corresponds to the time period during which said switchable valve is open, for determining the actual tidal volume TV and the ratio E/I of switchable-valve closed-time to open-time according to the relationships:

$TV = MV/R$ and $$\frac{E}{I} = \frac{F}{MV} - 1,$$

and when said target value $MV_T$ is larger than that MV value which corresponds to the combination of said target value for R and said maximum bellows tidal volume $TV_{max}$, for changing said actual frequency R away from said target value R to a frequency $R_A$ corresponding to the combination of said $TV_{max}$, and said MV target value, so that said target MV value is still actually realized according to $$R_A = \frac{MV_T}{TV_{max}}.$$

2. The ventilator system of claim 1 additionally comprising a display means connected to said microprocessor means for displaying at all times said actual minute volume MV, said actual frequency R and the actual expiration time to inspiration time ratio E/I.

3. The ventilator system of claim 1 wherein said electrically controllable variable throttling valve is comprised of an orifice leading from the input to the output of said valve, a conical plunger adapted for axial movement within said orifice to change the resistance to gas flow therein, a motor electrically connected to one of said microprocessor outputs, and a transmission means connected between said motor rotor and said valve plunger for translating the rotary motion of said motor effecting translational motion of said plunger.

4. The ventilator system of claim 3 wherein said throttling valve is additionally comprised of a mechanical to electrical transducer connected mechanically to said transmission means and connected electrically to said microprocessor for providing an electrical signal in said microprocessor that is directly related to the position of said plunger within said orifice and thus the gas flow resistance of said throttling valve.

* * * * *